(12) United States Patent
Ernst

(10) Patent No.: US 7,454,960 B2
(45) Date of Patent: Nov. 25, 2008

(54) HARDNESS TESTER WITH A LOADING STRUCTURE OF THE INDENTER INDEPENDENT OF THE STRESS FRAME CONNECTING THE INDENTER TO THE ANVIL

(75) Inventor: Alfred Ernst, Lugano (CH)

(73) Assignee: Erik Ernst, Casciago (IT)

( * ) Notice: Subject to any disclaimer, the term of this patent is extended or adjusted under 35 U.S.C. 154(b) by 150 days.

(21) Appl. No.: 10/573,304

(22) PCT Filed: Sep. 26, 2003

(86) PCT No.: PCT/IT03/00574

§ 371 (c)(1),
(2), (4) Date: Sep. 28, 2006

(87) PCT Pub. No.: WO2005/031314

PCT Pub. Date: Apr. 7, 2005

(65) Prior Publication Data

US 2007/0199371 A1    Aug. 30, 2007

(51) Int. Cl.
*G01N 3/42* (2006.01)
*G01N 3/48* (2006.01)

(52) U.S. Cl. .................. 73/81; 73/78; 73/79; 73/85

(58) Field of Classification Search ............... 73/73–85
See application file for complete search history.

(56) References Cited

U.S. PATENT DOCUMENTS

| | | | | | |
|---|---|---|---|---|---|
| 1,516,208 | A | * | 11/1924 | Rockwell | 73/83 |
| 1,646,195 | A | * | 10/1927 | German | 73/81 |
| 2,188,992 | A | * | 2/1940 | Wolpert et al. | 73/81 |
| 2,246,146 | A | * | 6/1941 | Smith | 73/83 |
| 2,319,208 | A | * | 5/1943 | Clark | 73/83 |
| 2,333,747 | A | * | 11/1943 | Sklar | 73/83 |
| 2,619,831 | A | * | 12/1952 | Sklar | 73/83 |

(Continued)

FOREIGN PATENT DOCUMENTS

GB         436185         10/1935

(Continued)

OTHER PUBLICATIONS

International Search Report No. PCT/IT03/00574, dated Aug. 4, 2004, 2 pages.

*Primary Examiner*—David A. Rogers
(74) *Attorney, Agent, or Firm*—Connolly Bove Lodge & Hutz LLP

(57) ABSTRACT

A hardness tester of a relatively large "cantilevering" and/or designed for permitting application of relatively large loads to the indenter may be constructed in a much slander and lighter manner by employing a loading mechanism based on the use of a second or auxiliary loading arm pivotally anchored to the frame of the tester and therefore completely independent of the stress structure of reference contained in the frame of the tester, which mechanical connects the anvil, on which the test object is placed, to the indenter. The load, applied to said second auxiliary arm is transmitted to the indenter carrying arm of the reference stress structure of the tester by unrestrained abutment of a rolling bearing solidly mounted on one of the two arms on a surface of the other arm. Along the trajectory of movement of the tip of the indenter toward the anvil.

4 Claims, 1 Drawing Sheet

U.S. PATENT DOCUMENTS

Figure 1:
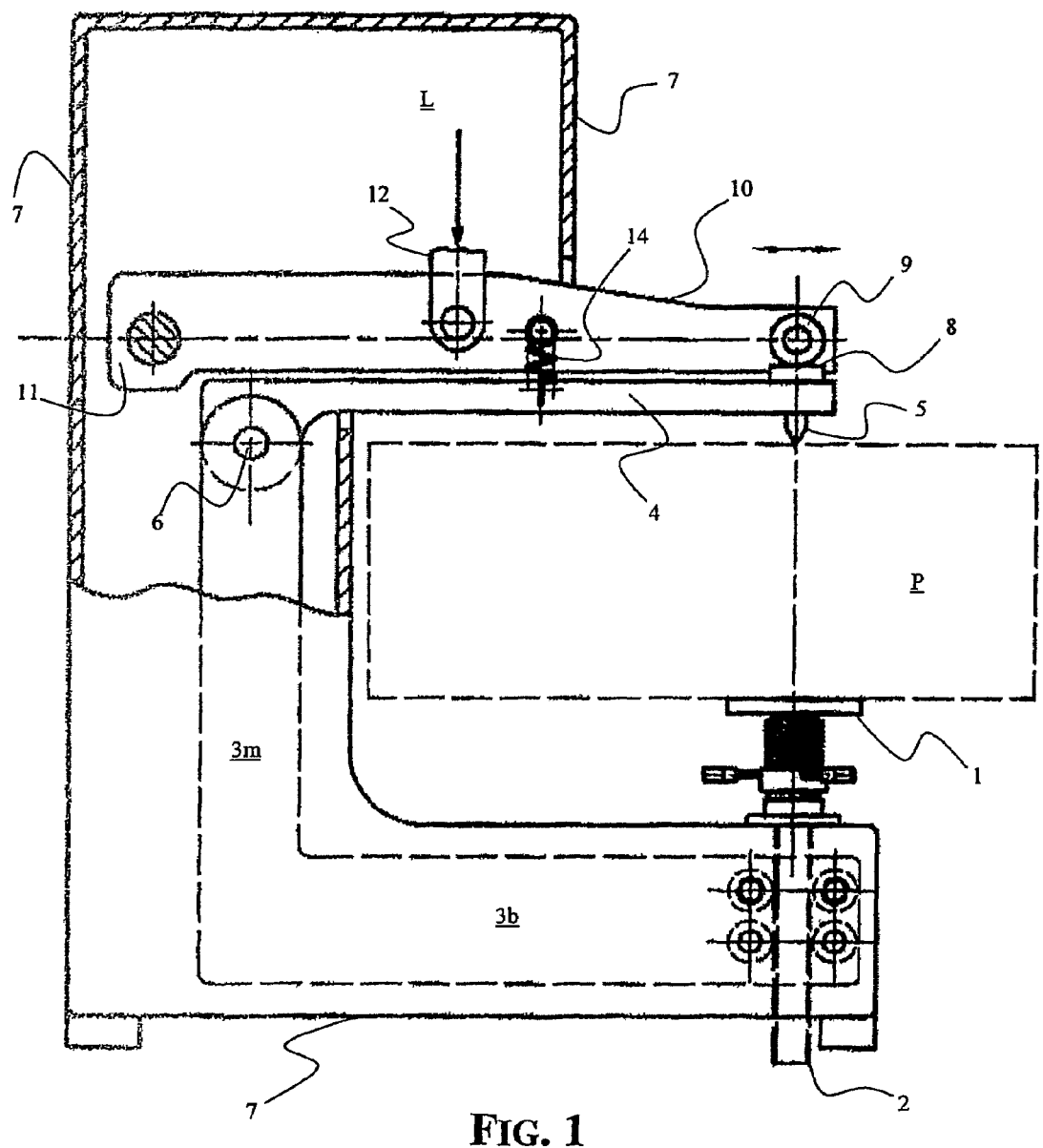

| | | | | |
|---|---|---|---|---|
| 2,640,591 A | * | 6/1953 | Sieggreen | 209/599 |
| 2,682,169 A | * | 6/1954 | Hohner | 73/83 |
| 2,752,779 A | * | 7/1956 | Clark | 73/83 |
| 2,804,769 A | * | 9/1957 | Clark, Sr. | 73/81 |
| 2,844,957 A | * | 7/1958 | Small | 73/83 |
| 2,892,344 A | * | 6/1959 | Sklar | 73/83 |
| 2,938,377 A | * | 5/1960 | Sklar | 73/83 |
| 3,365,937 A | * | 1/1968 | Miserocchi | 73/81 |
| 3,443,422 A | * | 5/1969 | Herzberg | 73/81 |
| 3,855,848 A | * | 12/1974 | Sidler | 73/81 |
| 3,949,600 A | | 4/1976 | Iwasaki | |
| 4,036,048 A | * | 7/1977 | Webster | 73/81 |
| 4,103,538 A | * | 8/1978 | Stoferle et al. | 73/81 |
| 4,118,975 A | * | 10/1978 | Iwasaki | 73/81 |
| 4,691,559 A | * | 9/1987 | Fischer | 73/81 |
| 5,309,754 A | * | 5/1994 | Ernst | 73/81 |
| 6,336,359 B1 | * | 1/2002 | Kawazoe et al. | 73/82 |
| 2004/0050149 A1 | * | 3/2004 | Kawazoe et al. | 73/81 |
| 2006/0288763 A1 | * | 12/2006 | Tsujii et al. | 73/81 |

FOREIGN PATENT DOCUMENTS

| | | |
|---|---|---|
| GB | 512520 | 9/1939 |
| GB | 1069365 | 5/1967 |
| JP | 56166447 A * | 12/1981 |
| SU | 1346970 A * | 10/1987 |

* cited by examiner

HARDNESS TESTER WITH A LOADING STRUCTURE OF THE INDENTER INDEPENDENT OF THE STRESS FRAME CONNECTING THE INDENTER TO THE ANVIL

The present invention relates to hardness testers that is to instruments used for determining the hardness of solid materials and finished mechanical components.

Hardness testers are instruments used in innumerable situations in order to control the quality of surface treatments, cladding materials, mechanical components of machines, metallic and nonmetallic laminates, castings and the like.

The structure of a hardness tester is well known and essentially consists of a frame having a robust stress structure mechanically connecting an anvil, onto which is sustained the object to be tested, to the indenter mounted on a pivoting arm of the stress structure. The pivoting arm carrying the indenter may be loaded with a certain load, sufficient to produce an indentation by the tip of the indenter on the surface of the object being tested.

It is evident as the stress structure must be dimensioned in such a way as to prevent flexions, in order to ensure a correct and reliable reference system for the forces and displacements that take place.

When testing relatively large mechanical pieces and/or when the area to be tested is relatively far away from the perimetral edge of the piece, the pivoting arm carrying the indenter must necessarily be sufficiently long that is it must look like a relatively long "cantilever".

This imposes the realization of stress structures particularly robust in order to ensure a substantial negligibility of flexions on the pivoting arm and/or on the rest of the stress structure.

These needs impose remarkable burdens in terms of increased weight and encumbrance of the test apparatus and of increased cost.

Of course, similar requirements arise in case the hardness tester must be able to permit the application of relatively high loads to the indenter (for the same "cantilevering").

There is therefore a clear need and utility of making hardness testers with a relatively large cantilevering and/or designed for uses that require the application of relatively high loads, without burdening them with an excessive increase of weight, encumbrance and cost as it is normally consequent to the need of providing them with a stress structure of enhanced rigidity in order to fulfill the primary requisite of substantial absence of nonnegligible flexions.

An excellent solution has now been found to these requisites.

It has been found that it is possible to realize a hardness tester for relatively high loads and/or with a relatively large "cantilevering" of the pivoted indenter carrying arm, without necessarily having to make the stress structure mechanically connecting the anvil to the indenter proportionately strong, by substantially rendering independent the loading means of the indenter from the stress structure of the hardness tester.

This important result is obtained by employing a purposely added second arm pivotally mounted on the apparatus frame and thus essentially independent from the stress structure of reference of the hardness tester.

Such a second or auxiliary arm transmits the load to the indenter carrying arm pivotally connected to the stress structure by bearing on it through an abutment established between a surface of one of the two pivotally held arms and a rolling bearing mounted on the other one of the two arms, the rolling axis of which orthogonally crosses the trajectory of movement of the indenter tip toward the anvil. The load is applied to the second or auxiliary arm through a pivotally mounted bracket.

Being the load transmitted to the indenter practically along the axis of the advancement of the indenter toward the anvil, the indenter bearing arm of the stress structure does not require to be mechanically dimensioned in function of the contemplated loads to avert flexions and even the remaining parts of the stress structures connecting the indenter to the anvil are much less stressed and may have relatively reduced cross sections and encumbrances.

The rolling bearing may be a ball or a roller bearing or any other equivalent device capable of moving (unrestrained) in respect of the surface of the other arm onto which it bears.

The attached FIGURE shows in a schematic manner a hardness tester made according to the present invention.

The hardness tester comprises an anvil 1, the height which may be adjusted in function of the thickness of the object P to be tested, by rotating the relative screw stem 2.

The anvil is solidly fixed to the base 3b of the stress structure of reference that connects the anvil 1 to the indenter 5 and which comprises the riser 3m and the arm 4, at the free end of which is mounted the indenter 5, and which is pivotally connected to the riser 3m of the stress structure by the pin 6.

Therefore, the arm 4 is free to oscillate in order to eventually permit to force the indenter 5 toward the anvil 1.

Of course, the height of the anvil is adjusted such to ensure that the movement of the tip of the indenter 5 during the loading phase of the indenter, in order to penetrate the material of the test sample P by a depth, often of the order of few micrometers, may be considered in practice as a linear movement along the axis of the indenter tip orthogonally incident on the plane of the anvil.

Of course, as any hardness tester, the stress structure is housed and rest on an apparatus frame, indicated with 7 as a whole.

According to the present invention, the load L that may be established by the use of weights or of elastic elements, is applied to the indenter 5 through the bearing on the surface of a force pad 8, for example of hardened steel, of a rolling bearing 9 mounted at the extremity of a second arm 10, which is pivotally anchored by the pin 11 to the frame 7 of the tester.

Of course, it is also possible of alternatively mounting the rolling bearing 9 on the indenter carrying arm 4 and establishing abutment with a bearing pad solidly connected to the second or auxiliary arm 10.

The load L is applied to this second oscillating arm 10, through a bracket 12, connected by a pin 13 to the second arm 10.

The pivotally held arm 4 carrying the indenter 5 is sustained by the spring 14 hanging from the auxiliary load arm 10.

The rolling bearing on the push pad 8, essentially decouples any out of axis force component from the indenter carrying arm 4.

As may be readily observed from the loading scheme of the mechanism according to the present invention shown in the FIGURE, the stress structure (of reference) is not directly involved in transmitting the load L to the indenter and therefore may retain a relatively light dimensioning even in case of a particularly large "cantilevering" (length of the indenter carrying arm 4).

In practice, the dimensioning of the reference stress structure 1, 3b, 3m and 4) is not directly tied to the length of the indenter carrying arm 4.

On the other hand, the correctness of the load that is effectively applied to the indenter 5 is safeguarded by correctly sizing the auxiliary arm 10 and the pin 11, and may in any case be ensured by a factory trimming of the hardness tester, carried out by establishing a biunivocal correspondence between values of the load L applied to the auxiliary arm 10 and the effective load value acting on the indenter 5, by employing, as it is commonly done suitable sensors (load cells).

This invention permits to construct hardness testers of relatively large "cantilevering" and/or suitable to permit the application of relatively high loads to the indenter that are outstandingly lighter than comparable testers built according to the known technique.

Of course, also the hardness tester made according to the present invention may avail itself of commonly used means for assessing or reading the hardness based upon the direct observation or displaying of the indentation produced by the indenter on the surface of the tested object in order to valuate its diameter, or upon an instrumental determination of the depth of the indentation (depth of penetration of the tip of the indenter during the loading phase).

The invention claimed is:

1. A hardness tester comprising an anvil for supporting an object to be tested, an indenter capable of producing an indentation on the surface of the object being tested and a load mechanism of the indenter comprising a robust stress structure of reference onto which is rigidly fixed said anvil and having at least an arm pivotally connected to the stress structure, carrying at the free end of which said indenter and means for applying a load onto said arm to force the indenter toward said anvil, characterized in that said means comprise a second arm pivotally connected to a frame of the hardness tester and capable of bearing on said first arm through an unrestrained abutment between a rolling bearing mounted on one of the two arms, the axis of rotation of which orthogonally crosses the trajectory of movement of the tip of said indenter toward said anvil, on a surface of the other arm;

the load being applied on said second arm pivotally connected to the frame through a pivotally held bracket and transmitted to said first arm carrying said indenter through said unrestrained bearing in coincidence with said trajectory of movement.

2. The hardness tester according to claim 1, wherein said rolling bearing is a ball or roller bearing.

3. The hardness tester according to claim 1, wherein said rolling bearing is mounted on said second arm and bears on the surface of a force pad solidly connected to said first arm.

4. The hardness tester according to claim 1, wherein said first arm is sustained by said second arm through a spring.

* * * * *